United States Patent [19]

George et al.

[11] Patent Number: 5,316,824

[45] Date of Patent: May 31, 1994

[54] TREATING BUILDING MATERIALS WITH A COMPOUND CONTAINING TIN COVALENTLY BONDED TO A SILYLATING GROUP

[75] Inventors: Billy L. George, Hudson, Wis.; Katherine A. Brown-Wensley, Lake Elmo, Minn.

[73] Assignee: Minnesota Mining and Manufacturing Company, St. Paul, Minn.

[21] Appl. No.: 808,364

[22] Filed: Dec. 16, 1991

[51] Int. Cl.$^5$ .................. B05D 1/18; B32B 21/02; D06N 7/04

[52] U.S. Cl. ...................... 428/145; 52/516; 427/393.6; 427/420; 427/421; 427/428; 427/430.1; 427/440; 428/141; 428/141 R; 428/144; 428/340; 428/341; 428/405; 428/406; 428/446; 428/447; 428/540; 428/703

[58] Field of Search ............ 427/387, 389.7, 393, 427/393.6, 420, 421, 428, 430.1, 440; 428/141, 142, 144, 145, 340, 341, 405, 406, 540, 543, 703, 446, 447; 52/516

[56] References Cited

U.S. PATENT DOCUMENTS

| | | | |
|---|---|---|---|
| 2,951,770 | 9/1960 | Lodge et al. | 117/100 |
| 3,395,164 | 7/1968 | Leebrick | 260/429.7 |
| 4,080,190 | 3/1978 | Law et al. | 71/67 |
| 4,160,846 | 7/1979 | Strunk et al. | 424/288 |
| 4,260,552 | 4/1981 | Strunk et al. | 260/429 |
| 4,578,489 | 3/1986 | Wehner et al. | 556/100 |
| 4,877,654 | 10/1989 | Wilson | 427/387 |
| 4,999,249 | 3/1991 | Deschler et al. | 428/447 |

FOREIGN PATENT DOCUMENTS 3828775 3/1990 Fed. Rep. of Germany.
61-233064 10/1986 Japan.
1565882 4/1980 United Kingdom.

OTHER PUBLICATIONS

Chemical Abstracts, vol. 112: 83008P, No. 10, Mar. 5, 1990, Columbus, Ohio, U.S.
Database WPIL, Week 8319, Derwent Publications Ltd., GB, Apr. 1983: AN 83-45880K and JP,A,58057460.
"Tributyltin-N,N-dialkyldithiocarbamates as Fungicides for Wood Preservation Against Rot", by J. Kizlink, *JOCCA* 74, No. 9, 1991, pp. 329-330.
"Tin", by G. Wilkinson, F. Stone and E. Abel, *Comprehensive Organometallic Chemistry*, Chpt. 11, vol. 2, pp. 530-535.
"Silane Coupling Agents", Edwin P. Pleuddemann, 2nd Edition, pp. 4–7, 31-37, 238-241.

*Primary Examiner*—Paul J. Thibodeau
*Assistant Examiner*—D. S. Nakarani
*Attorney, Agent, or Firm*—Gary L. Griswold; Walter N. Kirn; Jeffrey L. Wendt

[57] ABSTRACT

Building materials such as concrete can be protected from the growth of algae by being treated with a compound containing tin covalently bonded to a silylating group such that cleavage of the covalent bonds due to hydrolysis or photolysis is minimized, thus making the treatment ecologically safe. One such compound is (n-Bu)$_3$SnCH$_2$CH$_2$Si(OEt)$_3$. The tin compound can either be incorporated into raw materials from which building materials are to be made, or it can be applied to the finished building materials. When the tin compound is applied to a building material that is algae streaked, the streaking should disappear.

10 Claims, No Drawings

TREATING BUILDING MATERIALS WITH A COMPOUND CONTAINING TIN COVALENTLY BONDED TO A SILYLATING GROUP

BACKGROUND OF THE INVENTION

1. Field of the Invention

The invention is concerned with preserving the aesthetic appearance of architectural structures, e.g. buildings, freestanding walls, statuary and asphalt roofing shingles. More specifically, the invention concerns the treatment of building materials to prevent or remove disfiguring growths such as dark streaks of algae.

2. Description of the Related Art

Concrete provides durable, inexpensive building facings, roofing tiles and statuary, but can quickly develop dark streaks due to algae growth. Other building materials such as wood, limestone and other stonework, masonry, glass and asphalt roofing shingles likewise can become streaked by algae. The discoloration of asphalt roofing shingles is particularly noticeable when their roofing granules have a light color.

Concrete, stonework and masonry can be coated with silicones or silicates for water repellency, but such treatments do not prevent algae and other growths. Instead, it has been necessary to clean concrete periodically, usually with bleaches or phosphates, to remove algae growth. The cleaning operation is time-consuming and expensive and does nothing to inhibit recurring growth.

Algae growth on the granules of asphalt roofing shingles can be virtually eliminated by incorporating copper into the silicate binder that holds the color to the roofing granules. However, doing so substantially increases the cost of manufacturing the shingles. If copper could be incorporated into concrete, it might likewise inhibit algae growth, but copper would interfere with the setting up of the concrete. Another way to minimize algae growth on asphalt shingles is to minimize its content of limestone filler, but this can be economically undesirable.

OTHER PRIOR ART

Tin compounds can afford fungicidal wood protection as reported in Kizlink, "Tributyltin-N,N-dialkyldithiocarbamates as Fungicides for Wood Preservation Against Rot", JOCCA, Vol. 74, No. 9, 1991, pp 329–330. The Kizlink publication also cites prior publications concerning the application of tin compounds as corrosion inhibitors, fungicides for plastics, paper, and paper pulp, and as biocides. Unfortunately, tin compounds mentioned in the Kizlink publication are sufficiently soluble in water to release tin radicals which are potentially toxic. Because of this, it is believed that tin compounds have not been used commercially for treating wood or other building materials, although they have been used in marine paints where, until recently, there has been minimal concern for ecology.

German Offenlegungsschrift DE 3828775 (Huttinger) describes antimicrobial compounds for controlling undesirable growth of microbes in water-bearing devices, e.g., a device containing glass microbeads for disinfecting water. In the examples, glass microbeads impregnated with or coated with one of the antimicrobial compounds are tested for their ability to kill germs. Paper treated with one of the antimicrobial compounds is indicated to be useful for filtering bacteria from air. Huttinger's antimicrobial compounds include a class of tin compounds having a biocidal triorganotin moiety and silane moiety with affinity for adhesion to the water-bearing device. Those tin compounds would be useful in the present invention and come within the general Formula (I) disclosed below.

SUMMARY OF THE INVENTION

The invention concerns an economical, ecologically safe treatment that preserves the aesthetic appearance of architectural structures by preventing or removing disfiguring growths such as dark streaks of algae. The treatment not only affords such protection, but when applied to building materials that are streaked by algae, the streaking disappears and does not reappear. Building materials which should be effectively treated include concrete, wood, stonework, masonry, glass and asphalt roofing shingles or their granules. Because algae growth on wood can retain moisture and thus cause premature decay, the novel treatment should prolong the life of wood building materials such as wood shingles.

Briefly, the treatment involves applying to a building material an effective amount of a compound containing tin covalently bonded to a silylating group such that cleavage of the covalent bonds due to hydrolysis or photolysis is minimized, thus making the treatment ecologically safe. Useful compounds are of the general Formula (I):

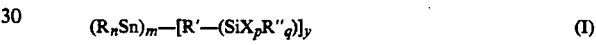

$$(R_nSn)_m\text{—}[R'\text{—}(SiX_pR''_q)]_y \qquad (I)$$

wherein

R is an organic radical within the formula $-CH_zH_{2z+1}$ wherein z ranges from 1 to 8, preferably from 3 to 6, and is more preferably 4

R' is a divalent radical of an aliphatic hydrocarbon containing 2 to 20 carbon atoms, preferably 2 to 8 carbon atoms, R'' is an organic radical, preferably alkyl, containing 1 to 8 carbon atoms, X is a hydrolyzable group such as halogen or an alkoxy, carboxy, or amino group containing 1 to 9 carbon atoms, preferably 1 to 2 carbon atoms, n is an integer from 0 to 3, preferably 2 or 3, p is an integer from 1 to 3, preferably 2 or 3, groups R, R', R'' and X may contain heteroatoms such as O or N, and they may be substituted with aryl, alkaryl or aralkyl groups. The groups R, R' and R'' may contain halogen such as F, Cl or Br as long as the bonds between Sn and Si are to tetracoordinate (sp³ hybridized) carbons which are not activated by the presence of heteroatoms. Any heteroatom and any aryl, alkaryl and aralkyl group in R'' should be separated from Sn and Si by two or more carbon atoms.

Specific examples of R include ethyl, n-propyl, iso-propyl, N-butyl, iso-butyl, sec-butyl, tert-butyl, n-pentyl, neo-pentyl, n-hexyl, n-octyl, iso-octyl, 4-(methoxy)-butyl, 4-chlorobutyl and 3,3,3-trifluoropropyl. Alkyl groups preferably are selected to minimize volatility and acute toxicity.

Specific examples of R' include ethane-1,2-diyl; propane-1,2-diyl; propane-1,3-diyl; butane-1,4-diyl; pentane-1,3,5-triyl; heptane-1,4,7-triyl; octane-1,3,5,7-tetrayl; 3-methoxypentane-1,5-diyl; 3-chloropentane-1,5-diyl; and 2-(trifluoropropyl)butane-1,4-diyl.

Specific examples of R'' include methyl, ethyl, n-propyl, iso-propyl, n-butyl, iso-butyl, sec-butyl, tert-butyl, n-pentyl, neo-pentyl, n-hexyl, n-octyl, iso-octyl, 4-(methoxy)butyl, 4-chlorobutyl and 3,3,3-trifluoropropyl.

Specific examples of X include fluoro, chloro, bromo, iodo, methoxy, ethoxy, iso-propyloxy, tert-butyloxy, acetoxy and dimethylamino. Preferred is alkoxy, especially ethoxy.

Specific examples of compounds of Formula (I) include $(n-Bu)_3SnCH_2CH_2Si(OEt)_3$, $(n-Bu)_3SnCH_2CH_2Si(OMe)_3$, $(n-Bu)_2Sn[(CH_2CH_2CH_2)Si(OEt)_3]_2$, $(n-Bu)_2Sn[(CH_2CH_2CH_2)Si(OMe)_3]_2$, $Sn[CH_2CH_2Si(OEt)_3]_4$, $Sn[(CH_2CH_2CH_2)Si(OEt)_3]_4$, $Et_3SnCH_2CH_2Si(OEt)_3$, $(n-propyl)_3SnCH_2CH_2CH_2Si(OEt)_3$, $(n-Bu)_3SnCH_2CH_2SiMe(OEt)_2$ and $(n-Bu)_3SnCH_2CH_2SiCl_3$. Preferred compounds are $(n)-Bu)_3SnCH_2CH_2Si(OEt)_3$ and $(n-Bu)_2Sn[(CH_2CH_2CH_2)Si(OEt)_3]_2$, and most preferred is $(n-Bu)_3SnCH_2CH_2Si(OEt)_3$ which is herein called "Formula (I-A)". Compounds of Formula (I) have no readily hydrolyzable groups linking the tin and the silylating group. That is, the bond between the R' group and each Sn and Si atom includes tetracoordinate carbon atoms that are not activated by the presence of heteroatoms or aryl, alkaryl or aralkyl groups. Furthermore, the R and R' groups are chosen to be chemically and photochemically unreactive and to minimize volatility and acute toxicity to mammals.

Compounds of Formula (I) preferably are prepared by either by the hydrostannylation of alkenylsilanes or by hydrosilation of alkenylstannanes. See A. G. Davies, P. J. Smith, "Tin," Chpt. 11 in G. Wilkinson, F. G. A. Stone, and E. W. Abel *Comprehensive Organometallic Chemistry*, Vol. 2, pp. 530–535, Pergamon Press: Oxford, 1982. Other methods include the reactions of organometallic reagents containing silicon such as Grignard reagents, organolithium reagents, organosodium reagents (including those formed in situ from organohalogens and sodium, the so-called Wurtz process), or organoaluminum reagents with stannyl or tin-containing organic halides, or the reactions of organometallic reagents containing tin with silyl or silicon-containing organic halides, or the acidolysis of stannylamines with silicon-containing hydrocarbon acids.

Compounds of Formula (I) may be prepared, stored, applied, and reacted with substrates as pure materials, as solutions in organic solvents such as alcohols (including methanol, ethanol and isopropanol), aromatic hydrocarbons (including toluene and xylene), ethers (including diethylether and tetrahydrofuran), or hydrocarbons (including hexane, cyclohexane, heptane and octane), as water-based or oil-based emulsions, or as mixtures with polymers and optionally solvent, optionally containing various additives.

Compounds of Formula (I) may be applied to any suitable substrate by means such as spraying, dipping, rolling, painting or brushing to the surfaces of small objects such as granules, beads and particles or to large objects such as buildings, statues and walls. Application may be performed in a highly controlled or controllable environment, such as laboratory or factory, or it may be performed in an environment subject to a large number of uncontrollable variables, such as an existing building, wall, statue or other edifice. The compounds may be caused to react, via the silylating agent, with such substrates at ambient or elevated temperatures (up to 300° C.) in the presence or absence of added catalyst. Their hydrolyzable X groups should react with surface hydroxyl groups of the building materials to form Si—O—linkages. The hydrolytic stability of the bond between compounds of Formula (I) and building materials is greater at higher values of the integer p.

Compounds of Formula (I) should be effective when applied to a building material in amounts as small as 0.01 g of tin ion per square meter of building material. To ensure ecological safety, they preferably are not used in amounts greater than 0.2 g/m$^2$ of tin ion. When used within those ranges on a building material that has algae growth, several months or more than a year may elapse before the algae disappears. When compounds of Formula (I) are instead applied to particulates such as roofing granules before the particulates are incorporated into a building material, they should be effective in amounts as small as 2 g of tin ion per cubic meter of the particulate material and preferably are not used in amounts exceeding 40 g/m$^3$ of tin ion.

Compounds of Formula (I) are useful for the treatment of roofing granules, prior to incorporation into a shingle or roof, to provide adhesion of the granule to asphalt and to retard algae growth. Before doing so, the granules should be heated to at least 50° C. to enhance adhesion of the compounds to the granules. Preferably the granules are preheated to 100°–125° C. Above 150° C. would be uneconomical, but the temperature could be as high as 250° C. without damage.

DESCRIPTION OF THE PREFERRED EMBODIMENTS

Objects and advantages of this invention are further illustrated by the following examples, but the particular materials and amounts thereof recited in these examples, as well as other and conditions and details, should not be construed to limit this invention.

SYNTHESIS OF COMPOUND OF FORMULA (I-A)

In an atmosphere of dry nitrogen, 99.8 g tributyltin hydride (Lancaster Synthesis, Windham, N.H., as supplied) and 71.0 g triethoxyvinylsilane (Petrarch Systems, Bristol, Pa., as supplied) were mixed with 0.13 g AIBN catalyst (Aldrich Chemical Co., Milwaukee, Wis., as supplied) added in three portions at 0, 3, and 6 hr reaction time. The reaction mixture was heated to 80°–85° C. for a total of 23 hr. Spectroscopic analysis of the mixture showed the reaction to be complete, and infrared, nuclear magnetic resonance $^1H$ and $^3C$), and mass spectral analysis and elemental analysis confirmed that the product is [2-(triethoxysilyl)ethyl]tributyltin or $(n-Bu)_3SnCH_2CH_2Si(OEt)_3$.

Environmental testing reported in the examples was carried out in Houston, Tex., which is at less than 30° latitude and has exceptionally high humidity. In the examples, all parts are by weight.

EXAMPLE 1

After adding to water 3 drops of sodium silicate per 100 ml of water, one part of the Compound of Formula (I-A) was added per 10 parts of water to provide "Water-based Emulsion (I-A)". An identical emulsion, except substituting mineral oil for the water, is here called "Oil-based Emulsion (I-A)".

Water-based Emulsion (I-A) was applied by paint roller to a portion of a clean north-facing concrete wall, using one pint per 100 ft$^2$ (51 ml/m$^2$), i.e., 0.1 g of tin ion per square meter of concrete. After one year, the uncoated portion of the wall had algae growth whereas the coated portion was free from algae.

Water-based Emulsion (I-A) was applied by paint roller to a portion of a north-facing panel having a 45° slope and bearing newly applied asphalt roofing shingles. To another portion was applied Oil-based Emulsion (I-A), each applied using one pint per 100 ft$^2$ (51 ml/m$^2$), or 0.1 g/m$^2$ of tin ion. After four years, the uncoated portion of the asphalt shingles had algae growth whereas both coated portions remained free from algae.

Water-based Emulsion (I-A) and Oil-based Emulsion (I-A) were applied by paint roller to different portions of a north-facing panel having a 45° slope and bearing asphalt roofing shingles that had a dark algae discoloration, again applying a 0.1 g/m$^2$ of tin ion. Within six months, the algae growth had disappeared from both coated portions whereas the uncoated portion retained the dark algae discoloration.

EXAMPLE 2

Roofing granules, as sold, conventionally have a mineral oil and silicone treatment which both controls dust and enhances adhesion to asphalt. To 100 parts of the mineral oil and 4 parts of the silicone was added 3 parts of the compound of Formula (I-A). Eleven parts of this modified treatment was added to an activated paint shaker containing 1000 parts of 3M roofing granules No. 93 (white) which had been pretreated to 110° C., and the shaking was continued for five minutes, thus applying ½ pint per ft$^3$ of granules or 17 g/m$^3$ of tin ion. After removal from the shaker, the coated granules were placed in an oven at 70° C. for one hour. These were then used in making asphalt roofing shingles from which circles 6.5 cm in diameter were cut. These circles were fitted into openings in a north-facing panel of asphalt shingles positioned at a 45° slope, which shingles were already discolored by algae.

After four years, the circles were free from algae.

For comparison, circles were cut from asphalt shingles that were identical except for omission of the compound of Formula (I-A). These showed algae streaks at 18 months and became almost totally discolored by algae at four years.

EXAMPLE 3

(Acute Toxicity)

The LD 50 for (n-Bu)$_3$SnCH$_2$CH$_2$Si(OEt)$_3$ was determined by International Bio Research (Hannover, West Germany) in a test performed according to the "OECD Principles of Good Laboratory Practice" in *Testing of Chemicals*, OECD (Paris, France, 1982). The acute oral toxicity was investigated in one group of fasted 5 male and 5 female Wistar rats. The animals were dosed once orally by stomach tube at 5 ml/kg of body weight. No mortalities were observed in 14 days, and no abnormal macroscopic findings in the cranial, thoracic, and abdominal cavities were observed in the animals necropsied on day 14. The LD 50 was determined to be greater than 5480 mg/kg of body weight.

What is claimed is:

1. Method of protecting roofing material comprised of roofing granule-bearing shingles against algae streaking by applying to the roofing granules prior to their incorporation into shingles an effective amount of a compound of the general formula (I):

$$(R_nSn)-[R'-(SiX_pR''_{p-3})]_{4-n} \quad (I)$$

wherein
R is an organic radical of the formula $C_zH_{2z+1}$ wherein z ranges from 1 to 8,
R' is a divalent radical of an aliphatic hydrocarbon containing 2 to 20 carbon atoms,
R" is an organic radical containing 1 to 8 carbon atoms,
X is a hydrolyzable group,
n is an integer from 0 to 3, and
p is an integer from 1 to 3.

2. Method as defined in claim 1, wherein R contains from 3 to 6 carbon atoms.

3. Method as defined in claim 1 wherein R' is a divalent radical of an aliphatic hydrocarbon containing from 2 to 8 carbon atoms.

4. Method as defined in claim 1 wherein R" is an alkyl group.

5. Method of protecting roofing material comprised of roofing granule-bearing shingles against algae streaking by applying to the roofing granules prior to their incorporation into shingles an effective amount of a compound of the general formula (I):

$$(R_nSn)-[R'-(SiX_pR''_{p-3})]_{4-n} \quad (I)$$

wherein
R is an organic radical of the formula $C_zH_{2z+1}$ wherein z ranges from 1 to 8,
R' is a divalent radical of an aliphatic hydrocarbon containing 2 to 20 carbon atoms,
R" is an organic radical containing 1 to 8 carbon atoms,
X is a hydrolyzable group,
n is an integer from 0 to 3, and
p is an integer from 1 to 3,
wherein X is selected from the group consisting of halogen and alkoxy.

6. Method as defined in claim 1 wherein the compound of general formula (I) is (n-Bu)$_3$SnCH$_2$CH$_2$Si(OEt)$_3$.

7. Method as defined in claim 1 wherein the roofing granules are at a temperature of at least 50° C. while the compound is being applied.

8. Method as defined in claim 1 wherein the compound is applied in an amount providing from 2 to 40 g of tin ion per m$^3$ of roofing granules.

9. A roofing shingle comprised of roofing granules incorporating an effective amount of a compound of the general formula (I):

$$(R_nSn)-[R'-(SiX_pR''_{p-3})]_{4-n} \quad (I)$$

wherein
R is an organic radical of the formula $C_zH_{2z+1}$ wherein z ranges from 1 to 8,
R' is a divalent radical of an aliphatic hydrocarbon containing 2 to 20 carbon atoms,
R" is an organic radical containing 1 to 8 carbon atoms,
X is a hydrolyzable group,
n is an integer from 0 to 3, and
p is an integer from 1 to 3.

10. Roofing shingle as defined in claim 9 wherein the compound provides from 2 to 40 g of tin ion per m$^3$ of roofing granules.

* * * * *

UNITED STATES PATENT AND TRADEMARK OFFICE
CERTIFICATE OF CORRECTION

PATENT NO.: 5,316 824

DATED: May 31, 1994

INVENTOR(S): Billy L. George and Katherine A. Brown-Hensley

It is certified that error appears in the above-identified patent and that said Letters Patent is hereby corrected as shown below:

Col. 2, line 30, "$(R_nSn)_m-[R'-(SiX_pR''_q)]_y$" should be --$(R_nSn)-[R'-SiX_pR''_{3-p})]_{4-n}$--.

Col. 2, line 34, "$-CH_zH_{2z+1}$" should be -- $-C_zH_{2z+1}$--.

Col. 2, line 46, "3," should be --3--.

Col. 2, line 47, "groups" should be --The groups--.

Col. 3, line 55, "painting or" should be --or--.

Col. 3, line 56, "beads and" should be --bead and--.

Col. 4, line 47, "$^3C$" should be --$^{13}C$--.

Signed and Sealed this

Twenty-ninth Day of July, 1997

Attest:

BRUCE LEHMAN

Attesting Officer

Commissioner of Patents and Trademarks